(12) United States Patent
Bobeck et al.

(10) Patent No.: US 9,790,134 B2
(45) Date of Patent: Oct. 17, 2017

(54) AGRICULTURAL MICROBIAL INOCULANT COMPOSITIONS AND USES THEREOF

(71) Applicant: Koch Agronomic Services, LLC, Wichita, KS (US)

(72) Inventors: Drew R. Bobeck, Doraville, GA (US); Cedric J. Pearce, Chapel Hill, NC (US)

(73) Assignee: Koch Agronomic Services, LLC, Wichita, KS (US)

( * ) Notice: Subject to any disclaimer, the term of this patent is extended or adjusted under 35 U.S.C. 154(b) by 0 days.

(21) Appl. No.: 15/170,813

(22) Filed: Jun. 1, 2016

(65) Prior Publication Data
US 2016/0355445 A1 Dec. 8, 2016

Related U.S. Application Data

(60) Provisional application No. 62/169,942, filed on Jun. 2, 2015.

(51) Int. Cl.
| | | |
|---|---|---|
| C05F 11/08 | (2006.01) | |
| C05G 3/00 | (2006.01) | |
| C05G 3/08 | (2006.01) | |
| A01N 63/00 | (2006.01) | |

(52) U.S. Cl.
CPC .............. *C05F 11/08* (2013.01); *A01N 63/00* (2013.01); *C05G 3/00* (2013.01); *C05G 3/0064* (2013.01); *C05G 3/08* (2013.01); *Y02P 60/218* (2015.11)

(58) Field of Classification Search
CPC .... C08L 2666/02; C08L 33/02; C08L 51/003; C08L 51/02; C08L 5/16; C08L 2666/26; C09D 151/003; C09D 151/02; A61L 15/20; A61L 15/46; A61L 15/60; A61L 2300/232; A61L 15/18; A61L 2300/802; A61L 11/00; A01N 63/00; A01N 25/04; C05F 11/08; C05G 3/00; C05G 3/0064; C05G 3/08

See application file for complete search history.

(56) References Cited

U.S. PATENT DOCUMENTS

| | | | |
|---|---|---|---|
| 4,000,258 A | 12/1976 | Shieh et al. | |
| 6,387,145 B1 | 5/2002 | Miele et al. | |
| 2012/0088667 A1* | 4/2012 | Williams | A01N 25/32 504/105 |
| 2014/0047882 A1 | 2/2014 | Gabrielson et al. | |
| 2014/0047883 A1 | 2/2014 | Gabrielson et al. | |
| 2015/0376163 A1* | 12/2015 | Kaiser | A01N 43/56 514/341 |

FOREIGN PATENT DOCUMENTS

| | | |
|---|---|---|
| CN | 1298854 A | 6/2001 |
| CN | 1314326 A | 9/2001 |
| CN | 1478761 A | 3/2004 |
| CN | 1163450 C | 8/2004 |
| CN | 1631855 A | 6/2005 |
| CN | 1241881 C | 2/2006 |
| CN | 101113120 A | 1/2008 |
| CN | 101209058 A | 7/2008 |
| CN | 101605741 A | 12/2009 |
| CN | 101774865 A | 7/2010 |
| CN | 101781141 A | 7/2010 |
| CN | 101875579 A | 11/2010 |
| CN | 102040435 A | 5/2011 |
| CN | 102452861 A | 5/2012 |
| CN | 102503734 A | 6/2012 |
| CN | 101875579 A | 5/2013 |
| CN | 103444782 A | 12/2013 |
| CN | 103553770 A | 2/2014 |
| CN | 103755498 A | 4/2014 |
| CN | 103787798 A | 5/2014 |
| CN | 103992180 A | 8/2014 |
| CN | 104016795 A | 9/2014 |
| CN | 102531804 A | 10/2014 |
| CN | 104098402 A | 10/2014 |
| CN | 104163718 A | 11/2014 |
| CN | 104163720 A | 11/2014 |
| CN | 104177172 A | 12/2014 |
| CN | 104222167 A | 12/2014 |
| CN | 104276906 A | 1/2015 |
| CN | 104291988 A | 1/2015 |
| CN | 104292007 A | 1/2015 |
| CN | 104326813 A | 2/2015 |
| CN | 104478616 A | 4/2015 |
| CN | 104609949 A | 5/2015 |
| EP | 406711 A | 1/1991 |
| EP | 0968980 B1 | 5/2010 |
| EP | 1323692 B1 | 8/2014 |
| GB | 2164640 A | 3/1986 |

(Continued)

OTHER PUBLICATIONS

International Search Report issued Jul. 20, 2016 for PCT Application No. PCT/US2016/035344.

Database WPI Week 201547; Thomas Scientific, London, GB; AN 2015-31864M, XP002759634.

Morris O N et al: "Chemical Additive Effects on the Efficacy of *Bacillus thuringiensisberlines* Subsp. Kurstaki Against Mamestra Configurata (Lepidoptera: Noctuidae)"; Journal of Economic Entomology, Entomological Society of America, Landham, Landham, MD, US; vol. 88, No. 4, Aug. 1, 1995 (Aug. 1, 1995), pp. 815-824, XP000535784, ISSN: 0022-0493; p. 816, col. 1, line 26-line 31, table 1.

Database WPI Week 201427; Thomson Scientific, London, GB; AN 2014-D29677; XP002759635.

(Continued)

*Primary Examiner* — Debbie K Ware

(57) ABSTRACT

The present disclosure provides novel agricultural microbial inoculant compositions for uses in promoting plant growth, plant productivity and/or soil quality. The novel microbial inoculant compositions comprise one or more microbial species, one or more urease inhibitors and/or one or more nitrification inhibitors. The present disclosure also provides fertilizer compositions comprising said microbial inoculant compositions.

28 Claims, No Drawings

(56) References Cited

FOREIGN PATENT DOCUMENTS

| GB | 2443892 A | 5/2008 |
|---|---|---|
| RU | 1713145 C | 2/1995 |
| RU | 2081583 C1 | 6/1997 |
| RU | 2149551 C1 | 5/2000 |
| WO | 9502695 A1 | 1/1995 |
| WO | 2014198840 A1 | 12/2014 |
| WO | 2015104698 A2 | 7/2015 |

OTHER PUBLICATIONS

Database WPI Week 200064; Thomson Scientific, London, GB; AN 2000-662770; XP002759636.

Database WPI Week 200874; Thomson Scientific, London, GB; AN 2008-M51033; XP002759637.

Database WPI Week 199808; Thomson Scientific, London, GB; AN 1998-084865; XP002759638.

Database WPI Week 201515; Thomson Scientific, London, GB; AN 2015-109842; XP002759639.

Oethinger, Margret, et al., Association of Organic Solvent Tolerance and Fluoroquinolone Resistance in Clinical Isolates of *Escherichia coli*, Journal of Antimicrobial Chemotherapy (1998) 41, 111-114, Center for Adaptation Genetics and Drug Resistance, and the Departments of Molecular Biology and Microbiology, and Department of Medicine, Tufts University School of Medicine and the New England Medical Center, Boston, MA 02111, USA; Section of Infectious Diseases and Clinical Immunology, University Hospital, Ulm, Germany.

Gao, Y., et al., Isolation and characterization of a novel organic solvent-tolerant *Anoxybacillus* sp. PGDY12, a thermophilic Gram-positive bacterium, Journal of Applied Microbiology, Journal of Applied Microbiology ISSN 1364-5072, 110, 472-478, Anhui Key Laboratory of Eco-engineering and Biotechnology, School of Life Sciences, Anhui University, Anhui, China, 2010.

\* cited by examiner

AGRICULTURAL MICROBIAL INOCULANT COMPOSITIONS AND USES THEREOF

CROSS-REFERENCE TO RELATED APPLICATION

This application claims priority to U.S. Provisional Patent Application No. 62/169,942, filed on Jun. 2, 2015, which is hereby incorporated by reference in its entirety.

TECHNICAL FIELD

The present disclosure relates to novel agricultural microbial inoculant compositions for uses in promoting plant growth, plant productivity and/or soil quality. The novel microbial inoculant compositions comprise one or more microbial species, one or more urease inhibitors and/or one or more nitrification inhibitors. The present disclosure also relates to fertilizer compositions comprising said microbial inoculant compositions, formulations and the uses thereof.

BACKGROUND

The use of fertilizers to enhance plant and crop production and overcome poor soil quality is widespread. Most commonly employed commercially available nitrogen containing fertilizers are inorganic chemical fertilizers such as urea. The extended use of urea is often associated with negative environmental consequences, such as nitrate contamination in run off and ground water, and emission of ammonia and nitrous oxide to the atmosphere. Attention to nitrogen fertilizer application has shifted from the role of promoting crop production to alleviating environmental pollution. There are a variety of new management practices and technologies that can promote nitrogen use efficiency and alleviate environmental pollution.

One of the widely used technologies is the application of a urease inhibitor in combination with the urea treatment. The urea component of fertilizer applied to the soil becomes a source of ammonia as a result of urease catalyzed hydrolysis of urea, an enzyme produced by numerous fungi and bacteria that is well known to skilled artisans. Urease inhibitors can slow down the conversion rate of urea to ammonia, thereby significantly reducing the quantity of urea that otherwise has to be applied on the soil by reducing the amount of ammonia volatilization. One of the most common urease inhibitors is N-(n-butyl) thiophosphoric triamide (NBPT) (See e.g. U.S. Pat. No. 5,698,003).

Another widely used technology is the application of nitrification inhibitors to significantly reduce nitrate leaching and gaseous nitrogen emissions. Most nitrogen supplied as a commercial fertilizer is ultimately transformed to a nitrate form of nitrogen. In the presence of adequate oxygen, warm temperatures, and some moisture, ammonium-N is converted to nitrate-N through a biochemical process known as nitrification that requires two forms of soil bacteria. The first bacterium *Nitrosomonas* converts ammonium-N to nitrite-N. The second bacterium *Nitrobacter* converts nitrite-N to nitrate-N. Nitrification inhibitors have one primary way of delaying the nitrification process by inhibiting the bacteria *Nitrosomonas* in the area where ammonium is to be present. Some widely used nitrification inhibitors that are commercially available include 2-chloro-6-(trichloromethyl)-pyridine (Nitrapyrin) and dicyandiamide (DCD).

In addition to the application of chemical enzyme inhibitors such as urease inhibitor N-(n-butyl) thiophosphoric triamide (NBPT) and nitrification inhibitors such as dicyandiamide (DCD), fertilizer compositions comprising microorganisms (so-called "bio-fertilizers" or "bio-stimulants") are increasingly considered as alternatives to conventional chemical fertilizers. The ability of specific bacterial species to promote plant growth has long been recognized. For example, nitrogen-fixing bacteria such as *Rhizobium* species provide plants with essential nitrogenous compounds. Species of *Azotobacter* and *Azospirillum* have also been shown to promote plant growth and increase crop yield, promoting the accumulation of nutrients in plants. However bacteria of these genera are often unable to compete effectively with native soil and plant flora, thereby requiring the application of impractically large volumes of inocula.

SUMMARY OF THE INVENTION

To date, urease inhibitors and nitrification inhibitors have met with varied success, while bio-fertilizers have typically met with limited success. Thus, there remains a need for improved fertilizers or fertilizer additives and methods that are effective in providing nutrients for plant growth and are environmentally safe and non-hazardous. One solution is to provide a combination of urease inhibitors and/or nitrification inhibitors with bio-fertilizers. Nevertheless, the combination of urease inhibitors and/or nitrification inhibitors with bio-fertilizers is not straight forward. First, urease inhibitors and/or nitrification inhibitors can weaken or kill the bio-fertilizers when combined. Second, urease inhibitors and/or nitrification inhibitors are typically dispensed in a solvent system (e.g. glycol, complex amines, aryl alcohols), which can also weaken or kill the bio-fertilizers.

WO 2015/104698 A2 disclosed combining a urease inhibitor with many microbial pesticides. However, it did not disclose any solvent system that could provide reasonable viability for the listed microbial pesticides. In addition, it did not identify any solvent-tolerant bacteria.

Solvent-tolerant bacteria are potentially useful in many applications of microbial transformation for environmental remediation as well as in biotechnological processes. Organic solvent tolerance may be a species-specific property and may not be easily predictable. See, for example, Association of organic solvent tolerance and fluoroquinolone resistance in clinical isolates of *Escherichia coli*. Anbu, P., *Journal of Antimicrobial Chemotherapy*, (1998) 41, 111-114. Most of the reported and well-studied solvent-tolerant bacteria are Gram-negative bacteria. Gram-negative bacteria have the advantage of having an additional outer membrane that protects the cytoplasmic membrane by reducing the periplasmic concentrations of harmful solvents to acceptable levels. Owing to the inherent disadvantage of lacking an outer membrane, only a few Gram-positive organisms have been reported to exhibit solvent tolerance. See, for example, Isolation and characterization of a novel organic solvent-tolerant *Anoxybacillus* sp. PGDY12, a thermophilic Gram-positive bacterium. Gao, Y., *Journal of Applied Microbiology*, 110, 472-478.

Surprisingly, in extensive efforts to identify solvent-tolerant bacteria to promote plant health, plant nutrition, and/or soil health, a few agriculturally beneficial Gram-positive organisms are identified to be viable in some selected organic solvents while some Gram-negative organisms are not viable in the same organic solvents. For example, tested Gram-positive organisms species *Bacillus amyloliquefaciens, Bacillus licheniformis, Bacillus thuringiensis* and *Bacillus pumilus* have demonstrated viability time range from at least 2 hours to at least 21 days in a solution with at least one of the organic solvents propylene glycol (PG), N-methyl-2-pyrrolidone (NMP), triethylene glycol monobutyl ether, glycerol, and dimethyl sulfoxide (DMSO). However, none of the tested agriculturally beneficial Gram-negative species *Pseudomonas fluorescens, Pseudomonas putida*, and *Pseudomonas chlororaphis* demonstrated viability in the tested organic solvents.

In one embodiment, the present disclosure provides an agricultural microbial inoculant composition comprising at least one microbial strain from one or more microbial species, and at least one active agent, wherein the active agent is a urease inhibitor or a nitrification inhibitor or a combination thereof, and further wherein the at least one microbial strain is present at an effective amount to promote plant health, plant nutrition, and/or soil health in the presence of the active agent.

In one embodiment, the present disclosure provides an agricultural microbial inoculant composition comprising:
  i. at least one agriculturally beneficial *Bacillus* species selected from the group consisting of *Bacillus amyloliquefaciens, Bacillus licheniformis, Bacillus thuringiensis, Bacillus pumilus*, and any combination thereof; and
  ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof.

In one embodiment, the present disclosure provides an agricultural microbial inoculant composition comprising:
  i. at least one agriculturally beneficial *Bacillus* species selected from the group consisting of *Bacillus amyloliquefaciens, Bacillus licheniformis, Bacillus thuringiensis, Bacillus pumilus*, and any combination thereof;
  ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and
  iii. a urease inhibitor selected from the group consisting of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, N-(2-nitrophenyl)phosphoric triamide, and any combination thereof.

In one embodiment, the present disclosure provides an agricultural microbial inoculant kit comprising:
Part A, wherein Part A comprises a urease inhibitor and at least one organic solvent, wherein said urease inhibitor is selected from the group consisted of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, N-(2-nitrophenyl)phosphoric triamide, and any combination thereof; and wherein said organic solvent is selected from the group consisting of propylene glycol (PG), N-methyl-2-pyrrolidone (NMP), triethylene glycol monobutyl ether, glycerol, dimethyl sulfoxide (DMSO), and any combination thereof; and
Part B, wherein Part B comprises at least one *Bacillus* species selected from the group consisting of *Bacillus amyloliquefaciens, Bacillus licheniformis, Bacillus thuringiensis, Bacillus pumilus*, and any combination thereof,
wherein each Part A and Part B is contained in a separate container.

In one embodiment, the present disclosure provides an agricultural microbial inoculant kit comprising:
Part A, wherein Part A comprises at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and
Part B, wherein Part B comprises at least one *Bacillus* species selected from the group consisting of *Bacillus amyloliquefaciens, Bacillus licheniformis, Bacillus thuringiensis, Bacillus pumilus*, and any combination thereof,
wherein each Part A and Part B is contained in a separate container.

In another embodiment, the present disclosure provides a method of enhancing a yield trait in a subject plant as compared to the yield trait of a reference or control plant, the method comprising contacting a subject plant, plant part, plant seed, or surrounding soil with an effective amount of a microbial inoculant composition of the present disclosure.

The urease inhibitor or nitrification inhibitor can mitigate nitrate contamination in run off and ground water, and the emission of a large amount of ammonia and nitrous oxide to the atmosphere. The microbial species can further promote plant health, plant nutrition, and soil health. The combination of both chemical enzyme inhibitors and microbial species in suitable compositions and formulations may serve as a better approach to improve the efficiency of nitrogen-based fertilizer usage by improving plant productivity, soil quality, and the overall environmental sustainability.

DETAILED DESCRIPTION OF THE INVENTION

Unless defined otherwise, all technical and scientific terms used herein have the same meaning as commonly understood by those of ordinary skill in the art.

In one embodiment, the present disclosure provides an agricultural microbial inoculant composition comprising at least one microbial strain from one or more microbial species, and at least one active agent, wherein the active agent is a urease inhibitor or a nitrification inhibitor or a combination thereof, and further wherein the at least one microbial strain promotes plant health, plant nutrition, and/or soil health in the presence of the active agent.

In another embodiment, the present disclosure provides an agricultural microbial inoculant composition comprising at least one microbial strain from one or more microbial species, and at least one active agent, wherein the active agent is a urease inhibitor or a nitrification inhibitor or a combination thereof, further wherein the at least one microbial strain promotes plant health, plant nutrition, and/or soil health in the presence of the active agent, wherein one or more microbial species are selected from the following group:
  (1) Spore forming species of bacteria;
  (2) Spore forming species of fungi;
  (3) Mycorrhizal organisms including *Laccaria bicolor, Glomus intraradices*, and *Amanita* species;
  (4) *Actinomyces* species and strains thereof, including *Streptomyces lydicus, Streptomyces griseoviridis, Streptomyces griseoviridis* K61 (Mycostop; AgBio development), and *Streptomyces microflavus* AQ 6121;

(5) *Bacillus* species and strains thereof, including: *Bacillus itcheniformis*; *Bacillus megaterium*; *Bacillus pumilus*, *Bacillus amyloliquefaciens*, *Bacillus licheniformis*; *Bacillus oleronius*; *Bacillus megaterium*; *Bacillus mojavensis*; *Bacillus pumilus*; *Bacillus subtilis*; *Bacillus circulans*; *Bacillus globisporus*; *Bacillus firmus*, *Bacillus thuringiensis*, *Bacillus cereus*, *Bacillus amyloliquefaciens* strain D747 (Double Nickel; Certis), *Bacillus firmus* strain I-1582 (Votivo and Nortica; Bayer), *Bacillus licheniformis*, *Bacillus licheniformis* strain SB3086 (EcoGuard; Novozymes), *Bacillus pumilus* strain GB34 (YieldShield; Bayer), QST2808 (Sonata; Bayer), *Bacillus subtilis* strains GB03 (Kodiak; Bayer), MBI 600 (Subtilex; Becker Underwood) & QST 713 (Serenade; Bayer), *Bacillus subtilis* strain GB122 plus *Bacillus amyloliquefaciens* strain GB99 (BioYield; Bayer), *Bacillus pumilus* strain BU F-33, *Bacillus thuringiensis galleriae* strain SDS-502, *Bacillus thuringiensis kurstaki*, VBTS 2546, *Bacillus cereus* BP01, *Bacillus subtilis* strain EB120, *Bacillus subtilis* strain J-P13, *Bacillus subtilis* FB17, *Bacillus subtilis* strains QST30002 and QST3004 (NRRL B-50421 and NRRLB-50455), *Bacillus subtilis* strains QST30002 and QST3004 (NRRL B-50421 and NRRLB-50455) sandpaper mutants, *Bacillus thuringiensis* subsp kurstaki strain VBTS 2477 quadruple enterotoxindeficient mutants, *Bacillus simplex* strains 03WN13, 03WN23 and 03WN25, *Bacillus subtilis* strain QST 713, *Bacillus mycoides* isolate BmJ NRRL B-30890, *Bacillus subtilis* strain DSM 17231 and *B licheniformis* strain DSM17236, *Bacillus aryabhattai*, *B. flexus*, *B. nealsonii*, *Bacillus sphaericus*, *Bacillus megaterium*, *B. vallismortis*, *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), and *Bacillus pumilus* (NRS-272);

(6) Species of "Plant Growth Promoting Rhizobacteria" (PGPRs) and strains thereof, including species reported to be capable of nitrogen fixation, for example *Gluconacetobacter* species (e.g. *Gluconacetobacter diazotrophicus* a.k.a. *Acetobacter diazotrophicus*), *Spirillum* species (e.g. *Spirillum lipoferum*), *Azospirillum* species, *Herbaspirillum seropedicae*, *Azoarcus* species, *Azotobacter* species, *Burkholderia* species, *Burkholderia* sp. A396, and *Paenibacillus polymyxa*;

(7) N-fixing bacterial species and strains thereof, including *Rhizobium* species (e.g. *Bradyrhizobium* species such as *Bradyrhizobium japonicum*, and *Rhizobium meliloti*);

(8) Microbial species and strains thereof that are known to improve nutrient use efficiency, including *Penicillium* species (e.g. *Penicillium bilaii*, *Penicillium bilaji*), and *Mesorhizobium cicero*;

(9) Microbial species and strains thereof that are known to have insecticidal or insect repellent effects including *Telenomus podisi*, *Baculovirus anticarsia*; *Trichogramma pretiosum*, *Trichogramma galloi*, *Chromobacterium subtsugae*, *Trichoderma fertile* JM41R, *Beauveria bassiana*, *Beauveria bassiana* strain NRRL 30976, *Beauveria bassiana* strain ATP02, DSM 24665, *Paecilomyces fumosoroseus*, *Trichoderma harzianum*, *Verticillium lecanii*, *Isaria fumosorosea* CCM 8367 (CCEFO.011.PFR), *Lecanicillium muscarium*, *Streptomyces microflavus*, and *Muscodor albus*;

(10) Microbial species and strains thereof that are known to have nematicidal effects e.g. *Myrothecium verrucaria*, *Pasteuria* species and strains thereof including *Pasteuria nishizawae*, *Pasteuria Pasteuria reneformis* strain Pr-3, *Paecilomyces lilacinus*, *Chromobacterium subtsugae*, *Pasteuria* strain ATCC SD-5832, *Metarhizium* species, and *Flavobacterium* species;

(11) Microbial species and strains thereof that are known to have antifungal, antimicrobial and/or plant growth promoting effects e.g. *Gliocladium* species, *Pseudomonas* species (e.g. *Pseudomonas fluorescens*, *Pseudomonas fluorescens* D7, *P. putida* and *P. chlororaphis*), *Pseudomonas fluorescens* strain NRRL B-21133, NRRL B-21053 or NRRL B-21102, *Pseudomonas fluorescens* VP5, *Pseudomonas synxantha*, *Pseudomonas diazotrophicus*, *Enterobacter cloacae* strain NRRL B-21050, *Trichoderma* species, *Trichoderma virens*, *Trichoderma atroviride* strains, *Coniothyrium minitans*, *Gliocladium* species, *Gliocladium virens*, *Gliocladium roseum* strain 321U, *Trichoderma harzianum* species, *Trichoderma harzianum Rifai*, *Clonostachys rosea* strain 88-710, *Pseudomonas rhodesiae* FERM BP-10912, *Serratia plymuthica* CCGG2742, *Cryptococcus lavescens* strain OH 182.9, *Serratia plymuthica*, *Cladosporium cladosporioides*, *Mitsuaria* species, *Coprinus curtus*, *Virgibacillus halophilus*, *Saccharomyces* species, *Metschnikovia fruticola*, *Candida oleophila*, *Acremonium* species, *Pseudozyma aphidis*, *Pythium oligandrum*, *Phoma* spp strain I-4278, *Achromobacter* species, *Geomyces* species, *Pseudomonas azotoformans*, strain F30A, *Brevibacillus parabrevis* strain No 4; non-toxigenic *Aspergillus* strains NRRL 50427, NRRL 50428, NRRL 50429, NRRL 50430 and NRRL 50431, *Sphaerodes mycoparasitica* strains IDAC 301008-01, -02, or -03, *Muscodor albus* strain NRRL 30547 or NRRL30548, *Serratia plymuthica* CCGG2742, *Pseudomonas koreensis* strain 101L21, *P lini* strain 131L01, *Pantoea agglomerans* strain 101L31, *Streptomyces scopuliridis* strain RB72, *Acremonium* spp endophytes, *Streptomyces* spp BG76 strain, *Paracoccus kondratievae*, *Enterobacter cloacae*, *Cryptococcus flavescens*, *Lactobacillus parafarraginis*, *Lactobacillus buchneri*, *Lactobacillus rapi* or *Lactobacillus zeae*, *Paenibacillus polymyxa*, *Serratia plymuthica*, *Phoma* species, *Pythium oligandrum*, *Mycosphaerella* species, and *Variovorax* species;

(12) Bacterial species and strains thereof from the group termed Pink-Pigmented Facultative Methylotrophs (PPFMs) including *Methylobacterium* species; and

(13) Microbial species and strains thereof that are known to have herbicidal effect e.g., *Pyrenophora semeniperda*;

wherein the urease inhibitor is selected from the group consisting of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, N-(2-nitrophenyl)phosphoric triamide, derivatives thereof, and any combination thereof; and wherein the nitrification inhibitor is selected from the group consisting of 2-chloro-6-trichloromethylpyridine, 5-ethoxy-3-trichloromethyl-1,2,4-thiadiazol, dicyandiamide, 2-amino-4-chloro-6-methyl-pyrimidine, 1,3-benzothiazole-2-thiol, 4-amino-N-1,3-thiazol-2-ylbenzene sulfonamide, thiourea, guanidine, 3,4-dimethylpyrazole phosphate, 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3-dihydro-2,2-dimethyl-7-benzofuranol methylcarbamate, N-(2,6-dimethylphenyl)-N-(methoxyacetyl)-alanine methyl ester, ammonium thiosulfate, 1-hydroxypyrazole, 3-methylpyrazole-1-carboxamide, 3-methylpyrazole, 3,5-dimethylpyrazole, 1,2,4-triazole, G77 Nitrification Inhibitor (CAS Registration No. 1373256-33-7), derivatives thereof, and any combination thereof.

In one embodiment, the present disclosure provides a solid carrier-based formulation for any microbial inoculant composition of the present disclosure, wherein the solid carrier is selected from mineral earths, e.g. silicates, silica gels, talc, kaolins, limestone, lime, chalk, clays, dolomite, diatomaceous earth, bentonite, montmorillonites; inorganic salts, e.g. aluminum sulfate, calcium sulfate, copper sulfate, iron sulfate, magnesium sulfate, silicon sulfate, magnesium oxide; polysaccharides, e.g. cellulose, starch; fertilizers, e.g., ammonium sulfate, ammonium phosphate, ammonium nitrate; products of vegetable origin, e.g. cereal meal, tree bark meal, wood meal, nutshell meal; grain flours suitable for the use in the present disclosure, e.g. flours from corn, rice, wheat, barley, sorghum, millet, oat, triticale, rye, buckwheat, fonio and *quinoa*, and mixtures thereof, In one embodiment, the present disclosure provides a solvent-based formulation for any agricultural microbial inoculant composition of the present disclosure, wherein the solvent is selected from alkanolamines such as triethanolamine, diethanolamine, monoethanolamine; alkyldiethanolamines, dialkylmonoethanolamines, wherein the alkyl group is $C_1$-$C_{24}$ branched or unbranched alkyl chain; dimethylsulfoxide (DMSO); alkylsulfones such as sulfolane (2,3,4,5-tetrahydrothiophene-1,1-dioxide); alkyl amides such as N-methylpyrrolidone, N-ethylpyrrolidone, or dimethylformamide; monoalcohols such as methanol, ethanol, propanol, isopropanol, or benzyl alcohol; glycols such as ethylene glycol, propylene glycol, diethylene glycol, or dipropylene glycol; glycol derivatives and protected glycols such as triethylene glycol monobutyl ether; glycerol and glycerol derivatives (trialcohols) including protected glycerols such as isopropylidine glycerol; dibasic esters and derivatives thereof; alkylene carbonates such as ethylene carbonate or propylene carbonate; monobasic esters such as ethyl lactate or ethyl acetate; polymers of carboxylic acids such as maleic acid, oleic acid, itaconic acid, acrylic acid, or methacrylic acid; monoalkyl glycol ethers and dialkyl glycol ethers; glycol esters; surfactants such as alkylbenzenesulfonates, lignin sulfonates, alkylphenol ethoxylates, or polyethoxylated amines.

In one embodiment, the present disclosure provides an encapsulated formulation for any agricultural microbial inoculant composition of the present disclosure. In the soil environment, inoculated microbial species can find survival difficult among naturally occurring competitor and predator organisms. To aid in survival of microorganisms present in microbial inoculants and fertilizer compositions of the present disclosure upon application in the environment, one or more of the microbial species strains may be encapsulated in, for example, a suitable polymeric matrix. In one example, encapsulation may comprise alginate beads such as has been described by Young et al, 2006, Encapsulation of plant growth-promoting bacteria in alginate beads enriched with humid acid, *Biotechnology and Bioengineering* 95:76-83. Those skilled in the art will appreciate that any suitable encapsulation material or matrix may be used. Encapsulation may be achieved using methods and techniques known to those skilled in the art. Encapsulated microorganisms can include nutrients or other components of the inoculant or fertilizer composition in addition to the microorganisms.

In one embodiment, the present disclosure provides an agricultural microbial inoculant composition comprising:
  i. at least one agriculturally beneficial *Bacillus* species selected from the group consisting of *Bacillus amyloliquefaciens, Bacillus licheniformis, Bacillus thuringiensis, Bacillus pumilus*, and any combination thereof; and
  ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof.

In one embodiment, the present disclosure provides an agricultural microbial inoculant composition comprising:
  i. at least one agriculturally beneficial *Bacillus* species selected from the group consisting of *Bacillus amyloliquefaciens, Bacillus licheniformis, Bacillus thuringiensis, Bacillus pumilus*, and any combination thereof;
  ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and
  iii. a urease inhibitor selected from the group consisting of N-(n-butyl)thiophosphoric triamide (NBPT), N-(n-butyl) phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, N-(2-nitrophenyl)phosphoric triamide, and any combination thereof.

In one embodiment, the present disclosure provides an agricultural microbial inoculant composition comprising:
  i. at least one agriculturally beneficial *Bacillus* species selected from the group consisting of *Bacillus amyloliquefaciens, Bacillus licheniformis, Bacillus thuringiensis, Bacillus pumilus*, and any combination thereof;
  ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and
  iii. a nitrification inhibitor selected from the group consisting of 2-chloro-6-trichloromethylpyridine, 5-ethoxy-3-trichloromethyl-1,2,4-thiadiazol, dicyandiamide, 2-amino-4-chloro-6-methyl-pyrimidine, 1,3-benzothiazole-2-thiol, 4-amino-N-1,3-thiazol-2-ylbenzene sulfonamide, thiourea, guanidine, 3,4-dimethylpyrazole phosphate, 2,4-diamino-6-trichloromethyl-5-triazine, poly etherionophores, 4-amino-1,2,4-triazole, 3-mercapto-1,2,4-triazole, potassium azide, carbon bisulfide, sodium trithiocarbonate, ammonium dithiocarbamate, 2,3-dihydro-2,2-dimethyl-7-benzofuranol methylcarbamate, N-(2,6-dimethylphenyl)-N-(methoxyacetyl)-alanine methyl ester, ammonium thiosulfate, 1-hydroxypyrazole, 3-methylpyrazole-1-carboxamide, 3-methylpyrazole, 3,5-dimethylpyrazole, 1,2,4-triazole, G77 Nitrification Inhibitor (CAS Registration No. 1373256-33-7), and any combination thereof.

In one embodiment, the present disclosure provides an agricultural microbial inoculant kit comprising:
Part A, wherein Part A comprises a urease inhibitor and at least one organic solvent, wherein said urease inhibitor is selected from the group consisted of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, N-(2-nitrophenyl)phosphoric triamide, and any combination thereof; and wherein said organic solvent is selected from the group consisting of propylene glycol (PG), N-methyl-2-pyrrolidone (NMP), triethylene glycol monobutyl ether, glycerol, dimethyl sulfoxide (DMSO), and any combination thereof; and Part B, wherein Part B comprises at least one *Bacillus* species selected from the group consisting of *Bacillus amyloliquefaciens, Bacillus licheniformis, Bacillus thuringiensis, Bacillus pumilus*, and any combination thereof, wherein each Part A and Part B is contained in a separate container.

In one embodiment, the present disclosure provides an agricultural microbial inoculant kit comprising:

Part A, wherein Part A comprises at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and Part B, wherein Part B comprises at least one *Bacillus* species selected from the group consisting of *Bacillus amyloliquefaciens, Bacillus licheniformis, Bacillus thuringiensis, Bacillus pumilus*, and any combination thereof, wherein each Part A and Part B is contained in a separate container.

In one embodiment, the at least one agriculturally beneficial *Bacillus* species in an agricultural microbial inoculant composition or a kit is selected from the group consisting of *Bacillus licheniformis, Bacillus thuringiensis*, and any combination thereof.

In one embodiment, the agriculturally beneficial *Bacillus* species in an agricultural microbial inoculant composition or a kit comprises *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof.

In one embodiment, the urease inhibitor in an agricultural microbial inoculant composition or a kit, where present, is N-(n-butyl)thiophosphoric triamide (NBPT).

In one embodiment, the nitrification inhibitor in an agricultural microbial inoculant composition or a kit, where present, is dicyandiamide, G77 Nitrification Inhibitor (CAS Registration No. 1373256-33-7), or a combination thereof.

In one embodiment, the solvent in an agricultural microbial inoculant composition or a kit comprises propylene glycol and N-methyl-2-pyrrolidone.

In one embodiment, the solvent in an agricultural microbial inoculant composition or a kit comprises propylene glycol, N-methyl-2-pyrrolidone, and triethylene glycol monobutyl ether.

In one embodiment, an agricultural microbial inoculant composition further comprises water, glycerol or a combination thereof.

In one embodiment, Part B of an agricultural microbial inoculant kit further comprises water, glycerol or a combination thereof.

In one embodiment, the present disclosure provides an agricultural microbial inoculant composition comprising:

i. at least one agriculturally beneficial *Bacillus* species selected from the group consisting of *Bacillus licheniformis, Bacillus thuringiensis*, and any combination thereof; and ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof.

In one embodiment, the present disclosure provides an agricultural microbial inoculant composition comprising:

i. at least one agriculturally beneficial *Bacillus* species selected from the group consisting of *Bacillus licheniformis, Bacillus thuringiensis*, and any combination thereof;

ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and iii. N-(n-butyl)thiophosphoric triamide (NBPT).

In one embodiment, the present disclosure provides an agricultural microbial inoculant kit comprising:

Part A, wherein Part A comprises N-(n-butyl)thiophosphoric triamide (NBPT) and at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and Part B, wherein Part B comprises at least one *Bacillus* species selected from the group consisting of *Bacillus licheniformis, Bacillus thuringiensis*, and any combination thereof, wherein each Part A and Part B is contained in a separate container.

In one embodiment, the present disclosure provides an agricultural microbial inoculant composition comprising:

i. at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof; and ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof.

In one embodiment, the present disclosure provides an agricultural microbial inoculant composition comprising:

i. at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof;

ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and iii. N-(n-butyl)thiophosphoric triamide (NBPT).

In one embodiment, the present disclosure provides an agricultural microbial inoculant composition comprising:

i. at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof;

ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and iii. dicyandiamide, G77 Nitrification Inhibitor (CAS Registration No. 1373256-33-7), or a combination thereof.

In one embodiment, the present disclosure provides an agricultural microbial inoculant kit comprising:

Part A, wherein Part A comprises N-(n-butyl)thiophosphoric triamide (NBPT) and at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and Part B, wherein Part B comprises at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof, wherein each Part A and Part B is contained in a separate container.

In one embodiment, the present disclosure provides an agricultural microbial inoculant kit comprising:

Part A, wherein Part A comprises at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof; and Part B, wherein Part B comprises at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof, wherein each Part A and Part B is contained in a separate container.

The weight percentage of a urease inhibitor such as NBPT in any embodiment of an agricultural microbial inoculant composition or a kit of the present disclosure, where presents, is in the range of 0.02-80%. In one embodiment, the weight percentage is in the range of 0.02-70%. In one embodiment, the weight percentage is in the range of 0.02-60%. In one embodiment, the weight percentage is in the range of 0.02-50%. In one embodiment, the weight percentage is in the range of 0.02-40%. In one embodiment, the weight percentage is in the range of 0.02-30%. In one embodiment, the weight percentage is in the range of 0.02-20%. In one embodiment, the weight percentage is in the range of 0.02-10%. In one embodiment, the weight percentage is in the range of 0.02-5%. In one embodiment, the weight percentage is in the range of 5-60%. In one embodiment, the weight percentage is in the range of 5-50%. In one embodiment, the weight percentage is in the range of 5-40%. In one embodiment, the weight percentage is in the range of 5-30%. In one embodiment, the weight percentage is in the range of 10-60%. In one embodiment, the weight percentage is in the range of 10-50%. In one embodiment, the weight percentage is in the range of 10-40%. In one embodiment, the weight percentage is in the range of 10-30%. In one embodiment, the weight percentage is in the range of 15-60%. In one embodiment, the weight percentage is in the range of 15-50%. In one embodiment, the weight percentage is in the range of 15-40%. In one embodiment, the weight percentage is in the range of 15-30%. In one embodiment, the weight percentage is in the range of 30-60%. In one embodiment, the weight percentage is in the range of 30-50%. In one embodiment, the weight percentage is in the range of 40-60%. The weight percentage is based on the entirety of the microbial inoculant composition.

The weight percentage of a nitrification inhibitor such as DCD, where present, in any embodiment of an agricultural microbial inoculant composition or a kit of the present disclosure is in the range of 1-80%. In one embodiment, the weight percentage is in the range of 1-70%. In one embodiment, the weight percentage is in the range of 1-60%. In one embodiment, the weight percentage is in the range of 1-50%. In one embodiment, the weight percentage is in the range of 1-40%. In one embodiment, the weight percentage is in the range of 1-30%. In one embodiment, the weight percentage is in the range of 1-20%. In one embodiment, the weight percentage is in the range of 1-10%. In one embodiment, the weight percentage is in the range of 1-5%. In one embodiment, the weight percentage is in the range of 10-80%. In one embodiment, the weight percentage is in the range of 10-70%. In one embodiment, the weight percentage is in the range of 10-60%. In one embodiment, the weight percentage is in the range of 10-50%. In one embodiment, the weight percentage is in the range of 10-40%. In one embodiment, the weight percentage is in the range of 10-30%. In one embodiment, the weight percentage is in the range of 20-80%. In one embodiment, the weight percentage is in the range of 20-70%. In one embodiment, the weight percentage is in the range of 20-60%. In one embodiment, the weight percentage is in the range of 20-50%. In one embodiment, the weight percentage is in the range of 20-40%. In one embodiment, the weight percentage is in the range of 20-30%. The weight percentage is based on the entirety of the microbial inoculant composition.

The weight percentage of an organic solvent such as propylene glycol (PG), N-methyl-2-pyrrolidone (NMP), triethylene glycol monobutyl ether, glycerol, dimethyl sulfoxide (DMSO), or any combination thereof in any embodiment of an agricultural microbial inoculant composition or a kit of the present disclosure is in the range of 20-99%. In one embodiment, the weight percentage is in the range of 20-90%. In one embodiment, the weight percentage is in the range of 20-80%. In one embodiment, the weight percentage is in the range of 20-70%. In one embodiment, the weight percentage is in the range of 20-60%. In one embodiment, the weight percentage is in the range of 20-50%. In one embodiment, the weight percentage is in the range of 30-99%. In one embodiment, the weight percentage is in the range of 30-90%. In one embodiment, the weight percentage is in the range of 30-80%. In one embodiment, the weight percentage is in the range of 30-70%. In one embodiment, the weight percentage is in the range of 30-60%. In one embodiment, the weight percentage is in the range of 30-50%. In one embodiment, the weight percentage is in the range of 40-99%. In one embodiment, the weight percentage is in the range of 40-80%. In one embodiment, the weight percentage is in the range of 40-70%. In one embodiment, the weight percentage is in the range of 40-60%. The weight percentage is based on the entirety of the microbial inoculant composition.

In one embodiment, an agricultural microbial inoculant composition or a kit of the present disclosure comprises propylene glycol with the weight percentage in the range of 40-70%, N-methyl-2-pyrrolidone with the weight percentage in the range of 15-40%, NBPT with the weight percentage in the range of 10-30%, and optionally a dye with the weight percentage in the range of 0.1-5%. The weight percentage is based on the entirety of the microbial inoculant composition.

In one embodiment, an agricultural microbial inoculant composition or an kit of the present disclosure comprises propylene glycol with the weight percentage in the range of 10-30%, N-methyl-2-pyrrolidone with the weight percentage in the range of 30-60%, NBPT with the weight percentage in the range of 15-40%, triethylene glycol monobutyl ether with the weight percentage in the range of 1-5%, and optionally a dye with the weight percentage in the range of 0-1%. The weight percentage is based on the entirety of the microbial inoculant composition.

In one embodiment, the concentration of the *Bacillus* species in the microbial inoculant composition of the present disclosure is at least $1.0 \times 10^2$ spores/mL. In one embodiment, the concentration is at least $1.0 \times 10^3$ spores/mL. In one embodiment, the concentration is at least $1.0 \times 10^4$ spores/mL. In one embodiment, the concentration is at least $1.0 \times 10^5$ spores/mL. In one embodiment, the concentration is at least $1.0 \times 10^6$ spores/mL. In one embodiment, the concentration is at least $1.0 \times 10^7$ spores/mL. In one embodiment, the concentration is at least $1.0 \times 10^8$ spores/mL. In one embodiment, the concentration is at least $1.0 \times 10^9$ spores/mL. In one embodiment, the concentration is at least $1.0 \times 10^{10}$ spores/mL. In one embodiment, the concentration is at least $1.0 \times 10^{11}$ spores/mL. In one embodiment, the concentration is at least $1.0 \times 10^{12}$ spores/mL. In one embodiment, the concentration is in the range of $1.0 \times 10^2$-$1.0 \times 10^{12}$ spores/mL. In one embodiment, the concentration is in the range of $1.0 \times 10^3$-$1.0 \times 10^{12}$ spores/mL. In one embodiment, the concentration is in the range of $1.0 \times 10^4$-$1.0 \times 10^{12}$ spores/mL. In one embodiment, the concentration is in the range of $1.0 \times 10^5$-$1.0 \times 10^{12}$ spores/mL. In one embodiment, the concentration is in the range of $1.0 \times 10^6$-$1.0 \times 10^{12}$ spores/mL. In one embodiment, the concentration is in the range of $1.0 \times 10^7$-$1.0 \times 10^{12}$ spores/mL. In one embodiment, the concentration is in the range of $1.0 \times 10^8$-$1.0 \times 10^{12}$ spores/mL. In one embodiment, the concentration is in the range of $1.0 \times 10^9$-$1.0 \times 10^{12}$ spores/mL.

In one embodiment of the present disclosure, the agricultural microbial inoculant composition may serve as a fertilizer by itself.

A dye may also be included in the agricultural microbial inoculant composition in the present disclosure. Any commonly used dye including food dyes may be used to provide visual evidence of the uniformity of the microbial inoculant composition. The weight percentage of a dye in the total microbial inoculant composition is 0-10%. In one embodiment, the weight percentage is 0.1-5%.

Examples of dyes suitable in the present disclosure include but are not limited to FD&C Blue No. 1, FD&C Blue No. 1, FD&C Green No. 3, FD&C Yellow No. 5, FD&C Red No. 3, FD&C Red No. 40, FD&C Yellow No. 6, and AGROTAIN® ULTRA green dye, or a combination thereof.

In another embodiment, the present disclosure provides a fertilizer composition comprising any agricultural microbial inoculant composition in any embodiment of the present disclosure, wherein the fertilize can be a granular fertilizer such as urea granular, a liquid fertilizer such as urea ammonium nitrate (UAN), an aqueous urea and ammonia nitrate aqueous solution, or anhydrous ammonia ($NH_3$).

In another embodiment, the present disclosure provides a method of enhancing a yield trait in a subject plant as compared to the yield trait of a reference or control plant, the method comprising contacting a subject plant, plant part, plant seed, or surrounding soil with an effective amount of an agricultural microbial inoculant composition of the present disclosure, wherein the microbial inoculant composition comprises:

i. at least one agricultural microbial strain from one or more microbial species, and ii. at least one active agent, wherein the active agent is a urease inhibitor, nitrification inhibitor, or a combination thereof, wherein the agricultural microbial inoculant composition at the effective amount is effective in enhancing the yield trait in the subject plant relative to the yield trait in the reference or control plant when the subject plant is contacted with the effective amount.

In another embodiment, the present disclosure provides a method for enhancing a yield trait in the plant, such as increasing plant growth and/or productivity, wherein the method comprises applying to the plant, plant part, plant seeds or to the soil in which the plant or plant seeds are grown an effective amount of an agricultural microbial inoculant composition of any embodiment of the present disclosure.

In another embodiment, the present disclosure provides a method for improving soil quality, wherein the method comprises applying to soil or to the plants or plant seeds in said soil an effective amount of an agricultural microbial inoculant composition as disclosed in any embodiment of the present disclosure.

In any embodiment of the disclosure, the concentrations of each agricultural microbial strain to be added to microbial inoculants and fertilizer compositions as disclosed herein will depend on a variety of factors including the identity and number of individual strains employed, the plant species being treated, the nature and condition of the soil to be treated, the exact nature of the microbial inoculant or fertilizer composition to be applied, the type and form of active agent, the form in which the inoculant or fertilizer is applied and the means by which it is applied, and the stage of the plant growing season during which application takes place. For any given case, appropriate concentrations should be effective in enhancing the yield trait in the presence of the active agent, and may be determined by one of ordinary skill in the art using only routine experimentation. By way of example only, the concentration of each strain present in the inoculant or fertilizer composition may be from about $1.0 \times 10^2$ colony forming units (CFU)/mL to about $5.0 \times 10^{12}$ CFU/mL per acre, from about $1.0 \times 10^2$ CFU/mL to about $5.0 \times 10^{10}$ CFU/mL per acre, from about $1.0 \times 10^2$ CFU/mL to about $5.0 \times 10^8$ CFU/mL per acre, from about $1.0 \times 10^2$ CFU/mL to about $5.0 \times 10^6$ CFU/mL per acre, or from about $1.0 \times 10^2$ CFU/mL to about $5.0 \times 10^4$ CFU/mL per acre.

In one embodiment of the present disclosure, a microbial food source such as kelp or glycerol may be included in any embodiment of the present disclosure.

The term "microbial species" refers to either naturally occurring or specifically developed variants or mutants of microbial species such as bacteria and fungi as disclosed herein. Variants or mutants may or may not have the same identifying biological characteristics of the specific strains exemplified herein, provided they share similar advantageous properties in terms of promoting plant growth and providing nutrients for plant growth in the soil. Variants of certain microbial strains may include but not limited to those developed by gene integration techniques such as those mediated by insertional elements or transposons or by homologous recombination, other recombinant DNA techniques for modifying, inserting, deleting, activating or silencing genes, intraspecific protoplast fusion, mutagenesis by irradiation with ultraviolet light or X-rays, or by treatment with a chemical mutagen such as nitrosoguanidine, methylmethane sulfonate, nitrogen mustard and the like, and bacteriophage-mediated transduction. Suitable and applicable methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); and J. Sambrook, D. Russell, *Molecular Cloning: A Laboratory Manual*, 3rd ed., Cold Spring Harbor Laboratory Press, Cold Spring Harbor, N.Y. (2001).

The term "plant productivity" or "yield trait" as used herein refers to any aspect of growth or development of a plant that is a reason for which the plant is grown. Thus, for purposes of the present disclosure, improved or increased "plant productivity" or "enhanced yield trait" refers broadly to improvements in biomass or yield of leaves, stems, grain, fruit, vegetables, flowers, or other plant parts harvested or used for various purposes, and improvements in growth of plant parts, including stems, leaves and roots.

The term "improving soil quality" refers to the increasing the amount and/or availability of nutrients required by, or beneficial to plants, for growth. For example only, such nutrients include nitrogen, phosphorous, potassium, copper, zinc, boron and molybdenum. Also encompassed by the term "improving soil quality" is reducing or minimizing the amount of an element that may be detrimental to plant growth or development such as, for example iron and manganese. Thus, improving soil quality by use of microbial inoculants and fertilizer compositions of the present disclosure thereby assists and promotes the growth of plants in the soil.

The term "effective amount" refers to an amount of microbial inoculant or fertilizer composition applied to a given area of soil or vegetation that is sufficient to promote one or more beneficial or desired outcomes, for example, in terms of plant growth rates, crop yields, or nutrient availability in the soil. An "effective amount" can be provided in one or more administrations. The exact amount required will vary depending on factors such as the identity and number of individual strains employed, the plant species being treated, the nature and condition of the soil to be treated, the exact nature of the microbial inoculant or fertilizer composition to be applied, the form in which the inoculant or fertilizer is applied and the means by which it is applied, and the stage of the plant growing season during which application takes place. For any given case, an appropriate "effective amount" may be determined by one with ordinary skill in the art using only routine experimentation.

The term "viability" in the present disclosure refers to the capability of repeated division of a microbial cell on an agar surface to produce a visible colony. The temperature for the viability evaluation is about 37° C. in the present disclosure. The viability time is counted from the moment a freshly prepared microbial culture in a nutrient broth is added to an organic solvent or a mixture of more than one organic solvent. After the microbial culture in a nutrient broth is added to the organic solvent or the mixture of more than one solvent, a small amount of mixture is taken out at certain time for incubation at about 37° C. The time period between the moment the microbial culture in a nutrient broth is added to an organic solvent and the moment that the mixture is taken out for incubation is defined as the viability time for the viability evaluation purpose.

Bacteria Viability Test in Solutions with Organic Solvents

The purpose of the bacteria viability test is to evaluate the viability of agriculturally beneficial bacteria species in solutions with organic solvents.

Both agriculturally beneficial Gram-positive and Gram-negative bacteria species are used for the test.

Agriculturally beneficial bacteria species were obtained from the American Type Culture Collection (ATCC), or the Agricultural Research Service Culture Collection. The bacteria species were grown on appropriate media, LB broth, nutrient broth, and checked microscopically with Gram staining and on Petri plates for purity. The bacteria species are pure, i.e., no unusual colonies were observed.

All the samples for testing are prepared by a two-step method.

First, selected agriculturally beneficial bacteria were grown overnight in Luria-Bertani (LB) medium at 37° C. with agitation. Growth was measured with a Bausch and Lomb Spectronic Spectrophotometer at at 600 nm ($OD_{600}$) to provide samples with cell optical density at 600 nm ($OD_{600}$) between 1.2 and 1.5. The overnight cultures typically contain $1.6 \times 10^8$ to $3.4 \times 10^8$ colony forming units per mL (CFU/mL).

Second, 0.5 mL of the prepared bacteria species sample in LB medium was added to an organic solvent or a mixture of organic solvents (4.5 mL).

A sample of 10 μL of the organic solvent solution with bacteria species is removed immediately for bacteria viability evaluation (T=0).

The remaining organic solvent solution with the bacteria species is incubated at 37° C. for future test. A volume of 10 μL of sample was taken out from the incubated organic solvent solution with the bacteria species at T=2 hours, 4 hours, 1 day, 2 days, 5 days, 7 days, 9 days, 12 days, 15 days, 18 days and 21 days for bacteria viability evaluation.

Each time the sample (10 μL) that was taken out for viability evaluation was placed onto agar plates, which was incubated overnight at 37° C. Colonies of bacteria present on the plates indicates that the bacteria have tolerated the solvent and was therefore viable. If there is no growth of colonies of bacteria, the bacteria have demonstrated no tolerance in the solvent.

The agriculturally beneficial bacteria that are viable for at least two hours from the moment that the bacteria sample is added to an organic solvent are considered to be viable in the organic solvent solution of the present invention.

*Bacillus amyloliquefaciens* (ATCC 23842) provided at least two hours of viability in NMP, and at least 5 days of viability in glycerol.

*Bacillus licheniformis* (ATCC 14580) provided at least one day of viability in triethylene glycol monobutyl ether, at least 5 days of viability in PG, at least 5 days of viability in NMP, at least 21 days of viability in glycerol, and at least 21 days of viability in DMSO.

*Bacillus licheniformis* (B-642) and *Bacillus licheniformis* (B-14368) each provided at least 21 days of viability in PG, at least 21 days of viability in NMP, at least 21 days of viability in triethylene glycol monobutyl ether, at least 21 days of viability in glycerol, and at least 21 days of viability in DMSO.

*Bacillus thuringiensis* (ATCC 10792) provided at least 2 hours of viability in PG, at least 2 hours of viability in NMP, at least 2 hours of viability in triethylene glycol monobutyl ether, at least 21 days of viability in glycerol, and at least 21 days of viability in DMSO.

*Bacillus thuringiensis* (HD-17) and *Bacillus thuringiensis* (HD-1) each provided at least 21 days of viability in PG, at least 21 days of viability in NMP, at least 21 days of viability in triethylene glycol monobutyl ether, at least 21 days of viability in glycerol, and at least 21 days of viability in DMSO.

*Bacillus pumilus* (NRS-272) provided at least 21 days of viability in PG, at least 21 days of viability in triethylene glycol monobutyl ether, at least 21 days of viability in glycerol, and at least 21 days of viability in DMSO.

Surprisingly, all three selected agriculturally beneficial Gram-negative species *Pseudomonas fluorescens* (ATCC 53958), *Pseudomonas putida* (ATCC 49128), and *Pseudomonas chlororaphis* (ATCC 55670), which were expected to have better solvent-tolerance, lost viability almost instantly when the prepared bacteria samples with $OD_{600}$ between 1.3 and 1.5 in nutrient broth were added to all tested organic solvent except glycerol.

The bacteria viability test in solutions with organic solvents in the present disclosure demonstrated that all the examples of *Bacillus licheniformis* and *Bacillus licheniformis* provided viability with time range from at least 2 hours to at least 21 days in a solution with at least one of the organic solvents PG, NMP, triethylene glycol monobutyl ether, glycerol and DMSO.

The bacteria viability test in solutions with organic solvents in the present disclosure demonstrated that the *Bacillus* strains *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1) and *Bacillus pumilus* (NRS-272) each provided viability with time range from at least 2 hours to at least 21 days in a solution with at least one of the organic solvents PG, NMP, triethylene glycol monobutyl ether, glycerol and DMSO.

Examples

TABLE 1

Examples with viability of at least 2 hours in at least one of the organic solvents PG, NMP, triethylene glycol monobutyl ether, glycerol or DMSO

| Example No. | *Bacillus* Species | *Bacillus* Strains | Solvent |
|---|---|---|---|
| 1 | amyloliquefaciens | ATCC 23842 | NMP |
| 2 | amyloliquefaciens | ATCC 23842 | Glycerol |
| 3 | licheniformis | ATCC 14580 | Triethylene glycol monobutyl ether |
| 4 | licheniformis | ATCC 14580 | PG |
| 5 | licheniformis | ATCC 14580 | NMP |
| 6 | licheniformis | ATCC 14580 | glycerol |
| 7 | licheniformis | ATCC 14580 | DMSO |
| 8 | licheniformis | B-642 | PG |
| 9 | licheniformis | B-642 | NMP |
| 10 | licheniformis | B-642 | Triethylene glycol monobutyl ether |
| 11 | licheniformis | B-642 | Glycerol |
| 12 | licheniformis | B-642 | DMSO |
| 13 | licheniformis | B-14368 | PG |
| 14 | licheniformis | B-14368 | NMP |
| 15 | licheniformis | B-14368 | Triethylene glycol monobutyl ether |
| 16 | licheniformis | B-14368 | Glycerol |
| 17 | licheniformis | B-14368 | DMSO |
| 18 | thuringiensis | ATCC 10792 | PG |
| 19 | thuringiensis | ATCC 10792 | NMP |
| 20 | thuringiensis | ATCC 10792 | Triethylene glycol monobutyl ether |
| 21 | thuringiensis | ATCC 10792 | Glycerol |
| 22 | thuringiensis | ATCC 10792 | DMSO |
| 23 | thuringiensis | HD-17 | PG |
| 24 | thuringiensis | HD-17 | NMP |
| 25 | thuringiensis | HD-17 | Triethylene glycol monobutyl ether |
| 26 | thuringiensis | HD-17 | Glycerol |
| 27 | thuringiensis | HD-17 | DMSO |
| 28 | thuringiensis | HD-1 | PG |
| 29 | thuringiensis | HD-1 | NMP |
| 30 | thuringiensis | HD-1 | Triethylene glycol monobutyl ether |
| 31 | thuringiensis | HD-1 | Glycerol |
| 32 | thuringiensis | HD-1 | DMSO |
| 33 | pumilis | NRS-272 | PG |
| 34 | pumilis | NRS-272 | Triethylene glycol monobutyl ether |
| 35 | pumilis | NRS-272 | Glycerol |
| 36 | pumilis | NRS-272 | DMSO |

What is claimed is:

1. A carrier-based agricultural microbial inoculant composition comprising:
   i. at least one agriculturally beneficial *Bacillus* species selected from the group consisting of *Bacillus amyloliquefaciens*, *Bacillus licheniformis*, *Bacillus thuringiensis*, *Bacillus pumilus*, and any combination thereof;
   ii. at least one organic solvent selected from the group consisting of propylene glycol (PG), N-methyl-2-pyrrolidone (NMP), triethylene glycol monobutyl ether, glycerol, dimethyl sulfoxide (DMSO), and any combination thereof, wherein the at least one organic solvent is present in an amount of 20-99 weight percent, based on the total weight of the microbial inoculant composition; and
   iii a urease inhibitor selected from the group consisting of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl) thiophosphoric triamide, N-(2-nitrophenyl)phosphoric triamide, and any combination thereof.

2. The agricultural microbial inoculant composition of claim 1, wherein the agriculturally beneficial *Bacillus* species is selected from the group consisting of *Bacillus licheniformis*, *Bacillus thuringiensis*, and any combination thereof.

3. The agricultural microbial inoculant composition of claim 1, wherein the agriculturally beneficial *Bacillus* species is selected from the group of strains consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof.

4. The agricultural microbial inoculant composition of claim 1, wherein the urease inhibitor is N-(n-butyl)thiophosphoric triamide (NBPT).

5. The agricultural microbial inoculant composition of claim 1, further comprising a nitrification inhibitor selected from the group consisting of 2-chloro-6-trichloromethylpyridine, 5-ethoxy-3-trichloromethyl-1,2,4-thiadiazol, dicyandiamide, 2-amino-4-chloro-6-methyl-pyrimidine, 1,3-benzothiazole-2-thiol, 4-amino-N-1,3-thiazol-2-ylbenzene sulfonamide, thiourea, guanidine, 3,4-dimethylpyrazole phosphate, 2,4-diamino-6-trichloromethyl-5-triazine, poly etherionophores, 4-amino-1,2,4-triazole, 3-mercapto-1,2,4-triazole, potassium azide, carbon bisulfide, sodium trithiocarbonate, ammonium dithiocarbamate, 2,3-dihydro-2,2-dimethyl-7-benzofuranol methylcarbamate, N-(2,6-dimethylphenyl)-N-(methoxyacetyl)-alanine methyl ester, ammonium thiosulfate, 1-hydroxypyrazole, 3-methylpyrazole-1-carboxamide, 3-methylpyrazole, 3,5-dimethylpyrazole, 1,2,4-triazole, G77 Nitrification Inhibitor (CAS Registration No. 1373256-33-7), and any combination thereof.

6. The agricultural microbial inoculant composition of claim 5, wherein the nitrification inhibitor is dicyandiamide, G77 Nitrification Inhibitor (CAS Registration No. 1373256-33-7) or a combination thereof.

7. The agricultural microbial inoculant composition of claim 1, wherein the weight percentage of the urease inhibitor is in the range of 0.02-80% based on the total weight of the agricultural microbial inoculant composition.

8. The agricultural microbial inoculant composition of claim 7, wherein the weight percentage of the urease inhibitor is in the range of 10-60%.

9. The agricultural microbial inoculant composition of claim 1, wherein the agriculturally beneficial *Bacillus* species has at least 2 hours of viability from the time when said agriculturally beneficial *Bacillus* species contacts said organic solvent.

10. The agricultural microbial inoculant composition of claim 1, wherein the agriculturally beneficial *Bacillus* species concentration is in the range of $1.0 \times 10^2$-$1.0 \times 10^{12}$ spores/mL.

11. The agricultural microbial inoculant composition of claim 1, further comprising a dye.

12. The agricultural microbial inoculant composition of claim 1, comprising propylene glycol and N-methyl-2-pyrrolidone.

13. The agricultural microbial inoculant composition of claim 12, wherein the weight percentage of propylene glycol is in the range of 40-70% based on the total weight of the agricultural microbial inoculant composition, the weight percentage of N-methyl-2-pyrrolidone is in the range of 15-40% based on the total weight of the agricultural microbial inoculant composition, the urease inhibitor is NBPT, and the weight percentage of NBPT is in the range of 10-30% based on the total weight of the microbial inoculant composition.

14. The agricultural microbial inoculant composition of claim 1 comprising propylene glycol, N-methyl-2-pyrrolidone, and triethylene glycol monobutyl ether.

15. The agricultural microbial inoculant composition of claim 14, wherein the weight percentage of propylene glycol is in the range of 10-30% based on the total weight of the agricultural microbial inoculant composition, the weight percentage of N-methyl-2-pyrrolidone is in the range of 30-60% based on the total weight of the agricultural microbial inoculant composition, the weight percentage of triethylene glycol monobutyl ether is in the range of 1-5% based on the total weight of the agricultural microbial inoculant composition, the urease inhibitor is NBPT, and the weight percentage of NBPT is in the range of 15-40% based on the total weight of the agricultural microbial inoculant composition.

16. A fertilizer composition comprising the agricultural microbial inoculant composition according to claim 1.

17. A method for promoting plant growth, plant productivity and/or soil quality, wherein the method comprises applying an effective amount of the agricultural microbial inoculant composition according to claim 1 to a plant, plant part, plant seed or soil.

18. An agricultural microbial inoculant kit comprising:
Part A, wherein Part A comprises a urease inhibitor and at least one organic solvent,
wherein said urease inhibitor is selected from the group consisting of N-(n-butyl)thiophosphoric triamide (NBPT), N-(n-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl) thiophosphoric triamide, N-(2-nitrophenyl)phosphoric triamide, and any combination thereof; and
wherein said organic solvent is selected from the group consisting of propylene glycol (PG), N-methyl-2-pyrrolidone (NMP), triethylene glycol monobutyl ether, glycerol, dimethyl sulfoxide (DMSO), and any combination thereof; and
Part B, wherein Part B comprises at least one *Bacillus* species selected from the group consisting of *Bacillus amyloliquefaciens, Bacillus licheniformis, Bacillus thuringiensis, Bacillus pumilus*, and any combination thereof,
wherein each of Part A and Part B is contained in a separate container, and
wherein the at least one organic solvent is present in an amount of 20-99 weight percent, based on the combined weight of Part A and Part B.

19. The agricultural microbial inoculant kit of claim 18, wherein Part B comprises at least one *Bacillus* species selected from the group consisting of *Bacillus licheniformis, Bacillus thuringiensis*, and any combination thereof.

20. The agricultural microbial inoculant kit of claim 18, wherein Part B comprises at least one agriculturally beneficial *Bacillus* strain selected from the group consisting of *Bacillus amyloliquefaciens* (ATCC 23842), *Bacillus licheniformis* (ATCC 14580), *Bacillus licheniformis* (B-642), *Bacillus licheniformis* (B-14368), *Bacillus thuringiensis* (ATCC 10792), *Bacillus thuringiensis* (HD-17), *Bacillus thuringiensis* (HD-1), *Bacillus pumilus* (NRS-272), and any combination thereof.

21. The agricultural microbial inoculant kit of claim 18, wherein the urease inhibitor is N-(n-butyl)thiophosphoric triamide (NBPT).

22. The agricultural microbial inoculant kit of claim 21, wherein Part A comprises propylene glycol and N-methyl-2-pyrrolidone.

23. The agricultural microbial inoculant kit of claim 22, wherein the weight percentage of propylene glycol is in the range of 40-70% based on the total weight of Part A, the weight percentage of N-methyl-2-pyrrolidone is in the range of 15-40% based on the total weight of Part A, and the weight percentage of NBPT is in the range of 10-30% based on the total weight of Part A.

24. The agricultural microbial inoculant kit of claim 21, wherein Part A comprises propylene glycol, N-methyl-2-pyrrolidone, and triethylene glycol monobutyl ether.

25. The agricultural microbial inoculant kit of claim 24, wherein the weight percentage of propylene glycol is in the range of 10-30% based on the total weight of Part A, the weight percentage of N-methyl-2-pyrrolidone is in the range of 30-60% based on the total weight of Part A, the weight percentage of triethylene glycol monobutyl ether is in the range of 1-5% based on the total weight of Part A, and the weight percentage of NBPT is in the range of 15-40% based on the total weight of Part A.

26. The agricultural microbial inoculant kit of claim 18, wherein the agriculturally beneficial *Bacillus* species has at least 2 hours of viability from the time when said agriculturally beneficial *Bacillus* species in Part A contacts said organic solvent in Part B.

27. The agricultural microbial inoculant kit of claim 18, wherein the weight percentage of the urease inhibitor is in the range of 0.02-80% based on the total weight of Part A.

28. The agricultural microbial inoculant kit of claim 18, wherein the agriculturally beneficial *Bacillus* species concentration is in the range of $1.0 \times 10^2$ to $1.0 \times 10^{12}$ spores/mL after Part A is mixed with Part B.

\* \* \* \* \*